US008317842B2

(12) United States Patent
Graham et al.

(10) Patent No.: US 8,317,842 B2
(45) Date of Patent: Nov. 27, 2012

(54) DISTAL TIBIA PLATING SYSTEM

(75) Inventors: Robert Graham, Miami, FL (US); Cesare Cavallazzi, Miramar, FL (US); Marcus Bourda, Miami, FL (US); G. Mark Lindsay, Fort Wayne, IN (US); Edward Mebarak, Miami, FL (US); Roy Sanders, Tampa, FL (US)

(73) Assignee: Biomet C.V., Gibraltar (GI)

( * ) Notice: Subject to any disclaimer, the term of this patent is extended or adjusted under 35 U.S.C. 154(b) by 711 days.

(21) Appl. No.: 11/948,277

(22) Filed: Nov. 30, 2007

(65) Prior Publication Data
US 2009/0143825 A1 Jun. 4, 2009

(51) Int. Cl.
*A61B 17/58* (2006.01)

(52) U.S. Cl. ....................................... 606/286

(58) Field of Classification Search .............. 606/61, 606/280–299, 246–279, 70, 71, 60
See application file for complete search history.

(56) References Cited

U.S. PATENT DOCUMENTS

| 4,573,458 | A | | 3/1986 | Lower |
| 5,015,248 | A | * | 5/1991 | Burstein et al. ............ 606/74 |
| 5,372,598 | A | | 12/1994 | Luhr et al. |
| 5,429,641 | A | | 7/1995 | Gotfried |
| 5,709,686 | A | | 1/1998 | Talos et al. |
| 5,718,704 | A | | 2/1998 | Medoff |
| 5,718,705 | A | * | 2/1998 | Sammarco ............... 606/284 |
| 5,785,711 | A | | 7/1998 | Errico et al. |
| 5,957,927 | A | * | 9/1999 | Magee et al. ............... 606/99 |
| 6,004,353 | A | | 12/1999 | Masini |
| 6,123,709 | A | | 9/2000 | Jones |
| 6,129,730 | A | | 10/2000 | Bono et al. |
| 6,206,881 | B1 | | 3/2001 | Frigg et al. |
| 6,652,530 | B2 | | 11/2003 | Ip et al. |
| 7,128,744 | B2 | | 10/2006 | Weaver |
| 7,179,260 | B2 | | 2/2007 | Gerlach et al. |
| 7,335,204 | B2 | * | 2/2008 | Tornier ..................... 606/284 |

(Continued)

FOREIGN PATENT DOCUMENTS
DE 434117 6/1995
(Continued)

OTHER PUBLICATIONS

Orthopaedic Surgery Essentials, Trauma, Chapter 28 "Tibial Plafond Fractures", copyright 2006 by Lippincott Williams & Wilkins.
(Continued)

*Primary Examiner* — Kevin T Truong
*Assistant Examiner* — Christopher Beccia
(74) *Attorney, Agent, or Firm* — Gordon & Jacobson, PC

(57) ABSTRACT

A distal tibia plating system includes anterolateral and medial plates. The anterolateral plate includes a shaft with both threaded first fastener holes and compression slots along its length. The head includes a first row of four threaded fastener holes arranged transversely to the longitudinal axis, a non-threaded compression screw hole, and a plurality of distal tabs. Each tab includes a ring with a single threaded fastener hole and a bridge that couples the ring to the distal end of the plate. The bridge is configured to bend preferentially in a desired direction and to allow tab removal. The medial plate is a low profile plate including a shaft and a relatively enlarged distal head. Several fasteners can be used with the plates. A plate holder is provided to maneuver the plates subcutaneously.

20 Claims, 15 Drawing Sheets

U.S. PATENT DOCUMENTS

| | | | |
|---|---|---|---|
| 7,341,589 B2* | 3/2008 | Weaver et al. | 606/291 |
| 7,527,639 B2* | 5/2009 | Orbay et al. | 606/287 |
| 2002/0045901 A1 | 4/2002 | Wagner et al. | |
| 2002/0058940 A1 | 5/2002 | Frigg et al. | |
| 2002/0128654 A1 | 9/2002 | Steger et al. | |
| 2004/0167522 A1* | 8/2004 | Niederberger et al. | 606/69 |
| 2005/0010226 A1* | 1/2005 | Grady et al. | 606/69 |
| 2005/0070904 A1 | 3/2005 | Gerlach et al. | |
| 2005/0085818 A1* | 4/2005 | Huebner | 606/69 |
| 2005/0090825 A1 | 4/2005 | Pfefferle et al. | |
| 2005/0187551 A1 | 8/2005 | Orbay et al. | |
| 2005/0261688 A1 | 11/2005 | Grady | |
| 2006/0004462 A1 | 1/2006 | Gupta | |
| 2006/0009771 A1 | 1/2006 | Orbay et al. | |
| 2006/0173458 A1* | 8/2006 | Forstein et al. | 606/69 |
| 2006/0217722 A1* | 9/2006 | Dutoit et al. | 606/69 |
| 2007/0233111 A1 | 10/2007 | Orbay et al. | |
| 2008/0300637 A1* | 12/2008 | Austin et al. | 606/290 |

FOREIGN PATENT DOCUMENTS

| | | |
|---|---|---|
| EP | 0486762 | 5/1992 |
| EP | 1464295 | 10/2004 |
| EP | 1654994 | 5/2006 |
| EP | 1707141 | 10/2006 |
| FR | 2406429 | 5/1979 |
| JP | 11299804 | 11/1999 |
| WO | WO 01/19267 | 3/2001 |
| WO | WO 03/007832 | 1/2003 |
| WO | WO2004/107957 | 12/2004 |

OTHER PUBLICATIONS

"Anterolateral and Medial Distal Tibia Locking Plates", smith &nephew PERI-LOC Periarticular Locked Plating System, Surgical Technique, Feb. 2005.

3.5 mm LCP Media Distial Tibia Plate Technique Guide, 2003 Synthes (USA).

LCP Anterolaterial Distial Tibia Plate 3.5 the low profile anatomic fixation system with optimal plate placement and angular stability. Technique Guide, Synthes 2007.

Zimmer Periarticular Distal Tibial Locking Plates, product brochure, 2005.

Summary of Safety and Effectiveness Information (510(k) Summary), Synthes USA, Jul. 29, 1998.

* cited by examiner

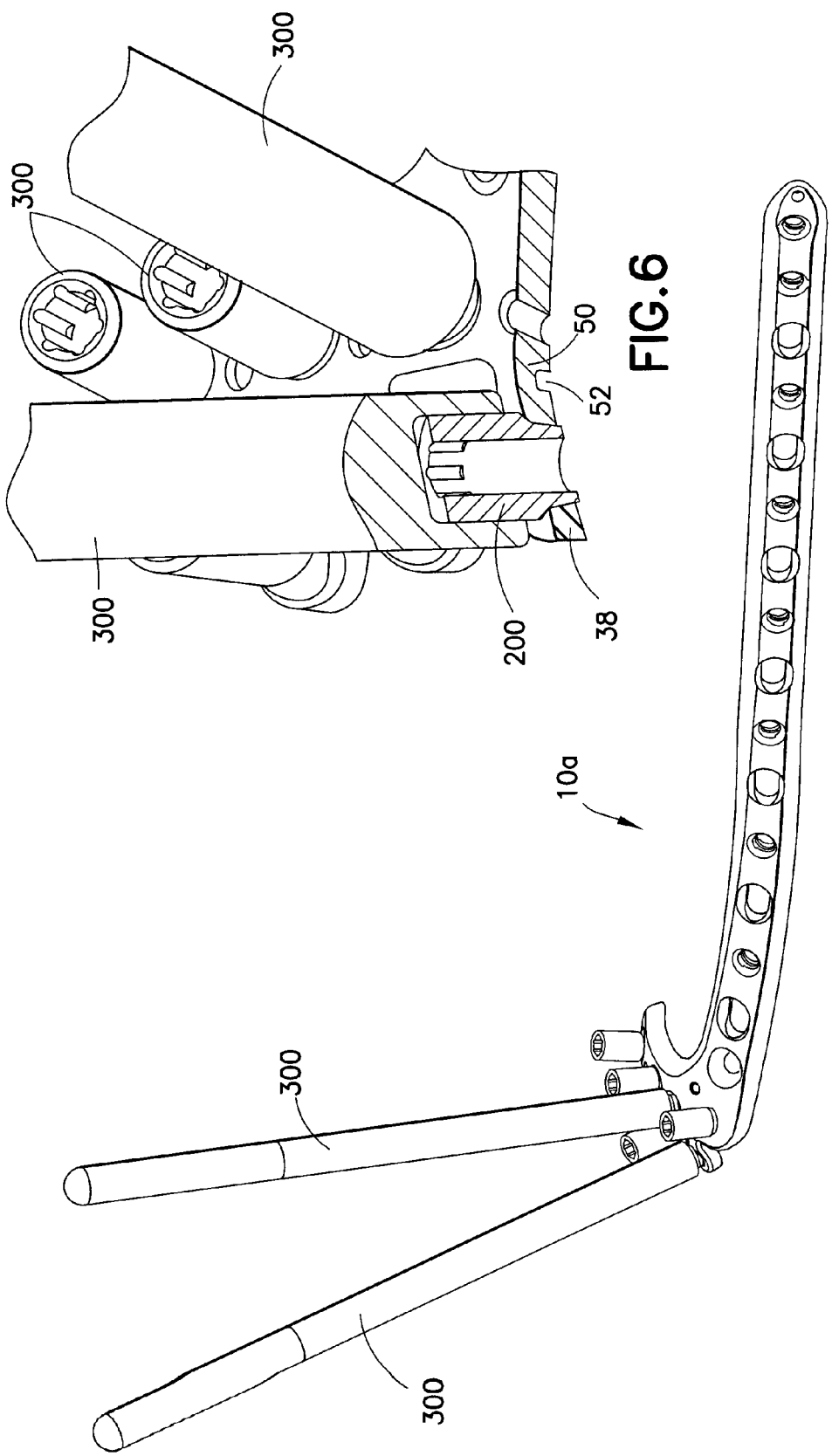

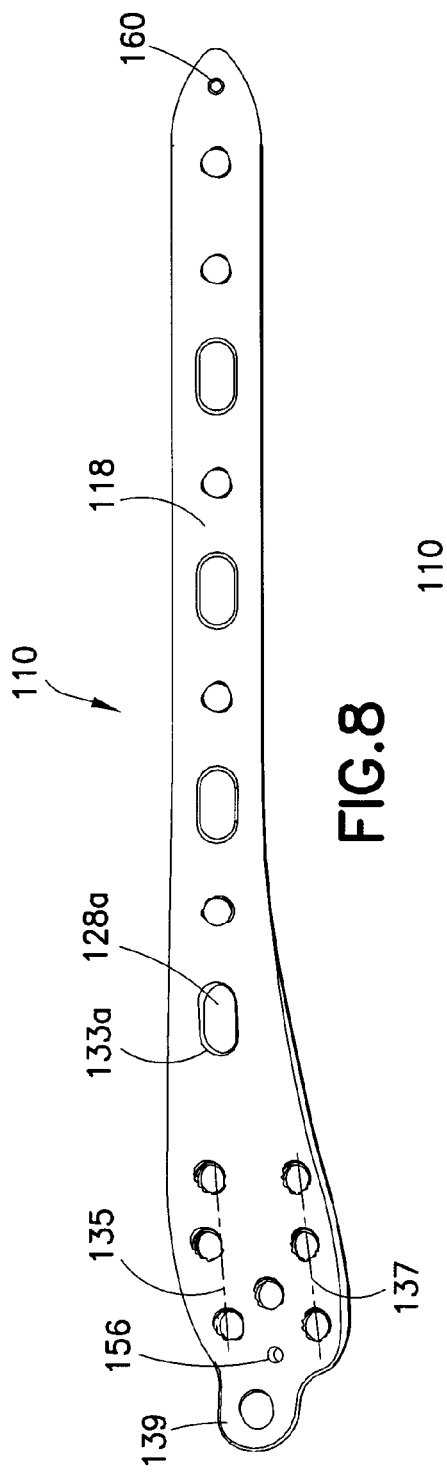
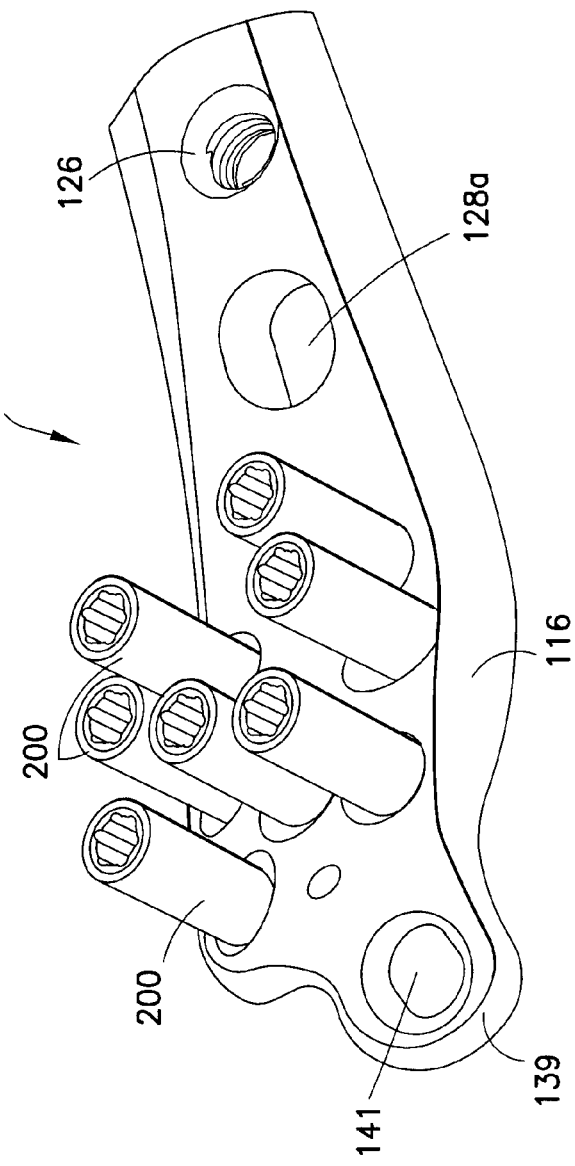

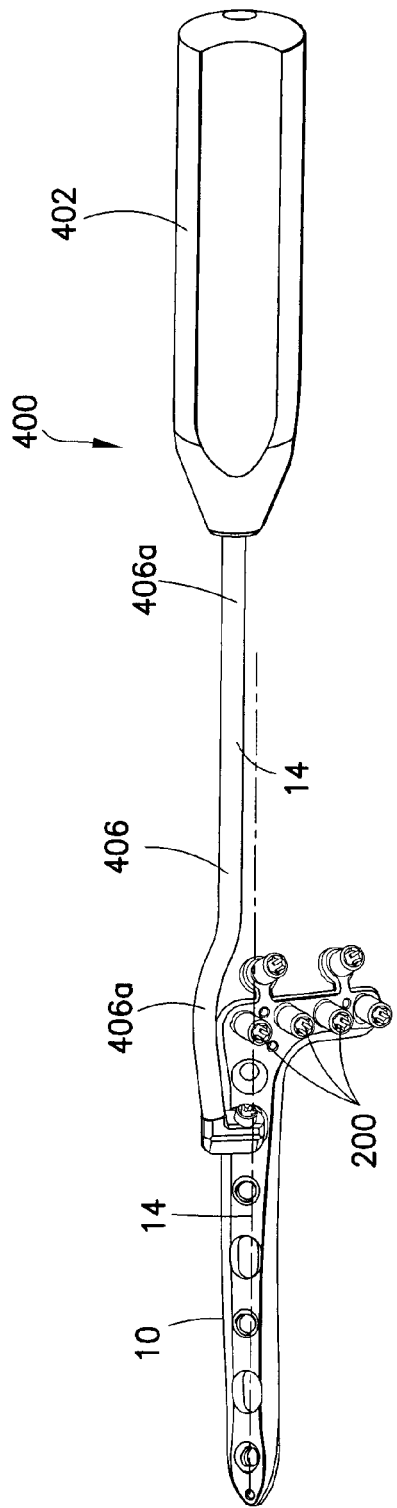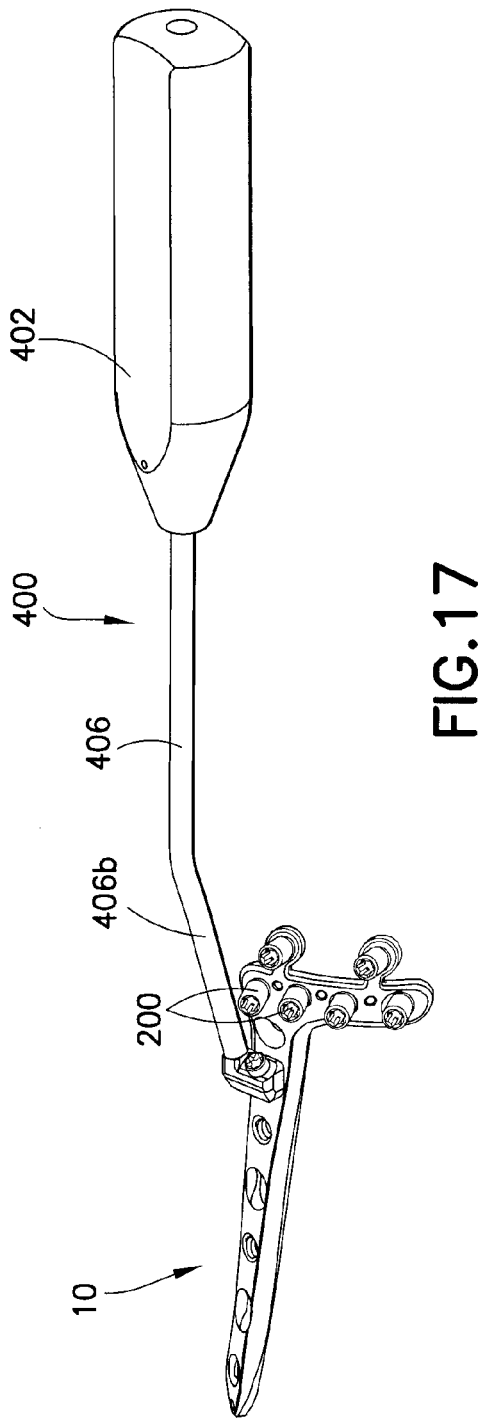

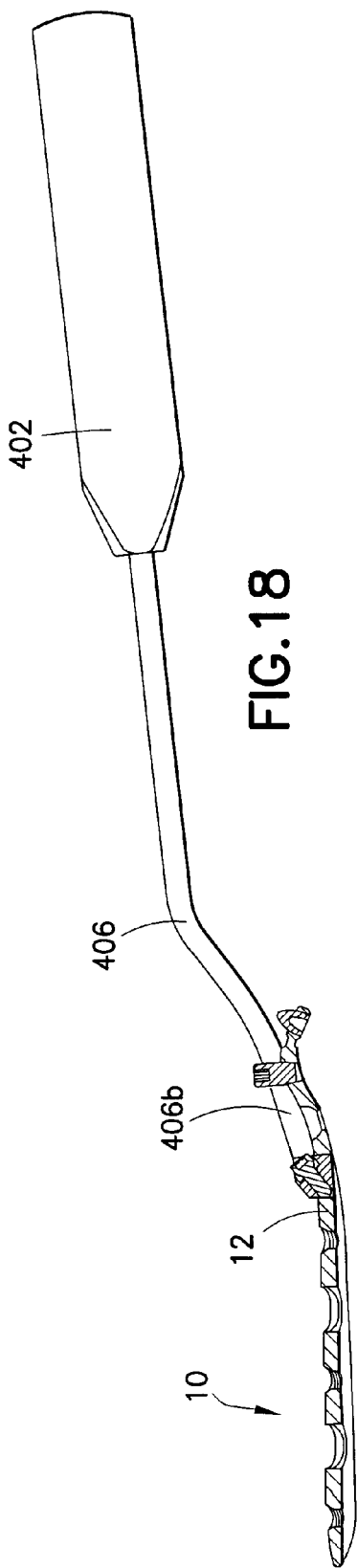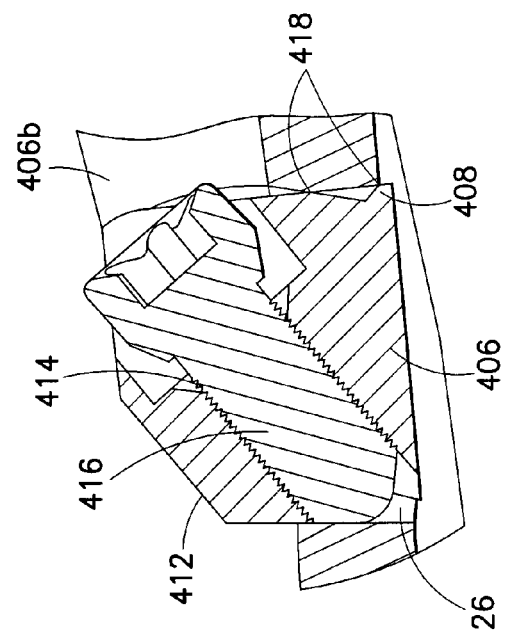

DISTAL TIBIA PLATING SYSTEM

BACKGROUND OF THE INVENTION

1. Field of the Invention

This invention relates broadly to surgical devices and methods for the internal fixation of fractured bones, and more particularly to bone plates, fasteners and tools therefor.

2. State of the Art

Fractures of the distal tibia include tibial plafond (or pilon) fractures and ankle fractures. These "high energy" fractures are typically caused by axial loading of the ankle joint, due to falls, motor vehicle accidents and sports. The more common ankle fractures are usually repaired with screw fixation. However, as with any kind of intra-articular fracture, distal tibial fractures are notoriously difficult to treat and are associated with a high complication rate.

Tibial plafond fractures are relatively uncommon (less than one percent of all fractures). Still, several thousands of people suffer annually. The type of fracture depends on the degree of comminution and displacement. Treatments of plafond fractures include external fixation, plating and nailing.

The same four basic principles for internal fixation apply to the distal tibia fracture as for any other bone fracture. These principles are proper anatomic reduction, stable fixation, preservation of blood supply and early, active mobilization. Before plating the distal tibia, surgeons usually wait several days after the injury was incurred to allow the soft tissues to heal and the swelling to decrease. Normally they will plate the distal fibula immediately if it is also fractured. After plating the distal tibia, weight bearing is normally not allowed for several days.

Currently there is some controversy among orthopedic surgeons concerning the management of tibial plafond fractures as to whether to use internal plating or external fixation. The trend in recent years has shifted to external fixation due to complications associated with plating. Major complications include skin sloughing and infection. These relate to the significant soft tissue injury associated with the fracture. Other less common complications include non-union, malunion, osteoarthritis and arthrodesis.

Current plates have been developed to try to reverse that trend. The plates include Synthes LCP Anterolateral and Medial Distal Tibia Plates 3.5, Smith & Nephew Peri-Loc Anterolateral and Medial Tibia Locking Plates, and Zimmer Periarticular Distal Tibia Locking Plates. The current plates are made of stainless steel. While the plates are pre-contoured for a non-specific bone, the systems are provided with bending tools that can be extended through the holes of a respective plate or gripped pliers that externally hold the plate to effect additional bending of the plate. However, such bending must be done with the plate off the bone in a manner in which it is difficult to approximate the shape of the plate to a specific bone without significant trial and error. In addition, the medial plates of current distal tibia fixation systems have limited support for the subchondral bone of the articular surface. Moreover, any such support is either at a pre-determined fixed angle using fixed angle screws in threaded holes or variable angle and under compression. Where surgeons want to use a distal tibia plating system with a fixed angle construct to support the fracture, fixed angle constructs do not conform to the anatomy or have the required strength to support distal tibia fractures. Thus, these plate systems are unacceptable in their limitations.

SUMMARY OF THE INVENTION

A distal tibia plating system according to the invention provides improvements in internal fixation of distal tibia fractures. The plating system includes an anterolateral plate and a medial plate. Each of the plates include a proximal shaft portion and a distal head portion. The head portion is provided with a plurality of threaded first holes and a non-threaded second hole. Each threaded first hole is configured for receiving at least one of a plurality of fastener types and is preferably chamfered to permit the head of the fastener to seat low in the hole. Each of the fastener holes is preferably provided with a pre-assembled drill guide that is adapted to guide a drill into bone in axial alignment with the fastener hole and optionally for use with one member of a pair of bending instruments.

The anterolateral plate is a low profile plate including a shaft defining a longitudinal axis and a laterally extending distal head. The shaft includes both threaded first fastener holes and compression slots along its length. The head includes a first row of four threaded fastener holes arranged transversely to the longitudinal axis, a non-threaded compression screw hole, and a plurality of distal tabs. Each tab includes a ring with a single threaded fastener hole and a bridge that couples the ring to the distal end of the plate. The hole in each tab is not necessarily chamfered, but the holes in the tabs are capable of receiving the same fasteners as the first row of threaded fastener holes. The holes in the tabs are aligned to define a second row of threaded holes. The first and second rows of threaded holes are approximately parallel and the axes of the threaded holes of the first row are staggered with respect to the axes of the threaded holes of the second row. The tabs are preferentially oriented such that the axes of threaded holes of the first row converge and pass between the axes of the threaded holes of the second row, with fasteners inserted therethrough thereby forming a load-bearing scaffold to support the articular surface of the distal tibia. The bridge of each tab is configured to bend preferentially in a desired direction, such that an axis of a fastener hole of a tab will not intersect the axis of a fastener hole in the first row of the distal head portion. In this manner, one or more of the tabs can be easily reconfigured relative to the remainder of the plate, e.g., to capture the distal rim of the tibia, to capture a specific bone fragment or buttress and support a desired area, while the plate is on the bone. This is performed while the plate is either on or off the bone, by coupling the bending instruments to the drill guides and applying a relative force to bending the tabs about the bridges. A tab may also be easily removed by using the bending tools to reverse bend the tab until a clean fracture of the bridge element is effected.

The medial plate is a low profile plate including a shaft and a relatively enlarged distal head. The shaft includes both threaded fastener holes and compression slots along its length. The most distal slot includes a distal undercut. The head includes preferably seven threaded fastener holes having preferably parallel axes, and preferably arranged in two parallel proximal-distal rows of three and a final hole located along the longitudinal axis of the plate between the two rows. At the distal end of the head, the head includes an extension provided with a non-threaded, non-circular hole.

Each of the plates further includes fixed angle K-wire alignment holes to receive K-wires for provisional fixation of bone fragments and for fluoroscopic confirmation of the location of the plate. K-wires are preferably provided in the system for use with the plates.

A plate holder is also provided which couples to the plates to maneuver the plates subcutaneously through a minimally invasive surgical incision. The plate holder includes a proximal handle, a distal mount, and an arm extending between the handle and the mount. The mount includes a first portion which seats within a slot on the shaft of either plate, and a second portion at which the shaft is coupled and which includes a tapered proximal side. A set screw hole is provided through the first and second portions, and a set screw is provided therein. When the first portion is seated in a compression slot of a plate shaft and the set screw is driven to seat, the set screw locks the mount to the plate shaft. The arm of the plate holder is contoured to seat closely to the head of the plate, but to clear the drill guides in the head portion of the plates. The plate holding tool facilitates percutaneous introduction of the plate, positioning of the plate on the bone surface and holding the plate while the first fastener is inserted.

Each fastener includes a shank portion for engagement into the bone, wherein the shank portion may have one of a cortical thread, a cancellous thread, a non-threaded portion and combinations thereof. The head portion of the fastener may have one of a fixed angle locking head, a non-locking compression head and a multidirectional locking head.

In view of the above, the system facilitates subchondral support of the articular surface so that plate shares the load with bone during healing. The system also facilitates bone targeting and contouring of the plates to the bone so that intra-articular fragments can be captured and fixated. The system accomplishes this in a manner that is low profile to minimize soft tissue trauma and patient discomfort.

Additional objects and advantages of the invention will become apparent to those skilled in the art upon reference to the detailed description taken in conjunction with the provided figures.

BRIEF DESCRIPTION OF THE DRAWINGS

FIG. 5 is a perspective view of another embodiment of an anterolateral plate the distal tibia system of the invention, shown with drill guides and bending tools.

FIG. 6 is an enlarged section view illustrating the structure of the distal head of the anterolateral plate and the attachment of the bending tools to the guides.

FIG. 8 is a bottom perspective view of the medial plate of FIG. 7.

FIG. 9 is an enlarged top distal perspective distal view of medial plate, shown with drill guides attached thereto.

FIG. 16 is an anterolateral view of the anterolateral plate and plate holder assembly.

FIG. 17 is a distal perspective view of the assembly of FIG. 16.

FIG. 18 is section view through the longitudinal axis of the anterolateral plate of the assembly of FIG. 16.

FIG. 19 is an enlarged section view through the coupling of the plate holder to the anterolateral plate.

DETAILED DESCRIPTION OF THE PREFERRED EMBODIMENTS

Figure 1:
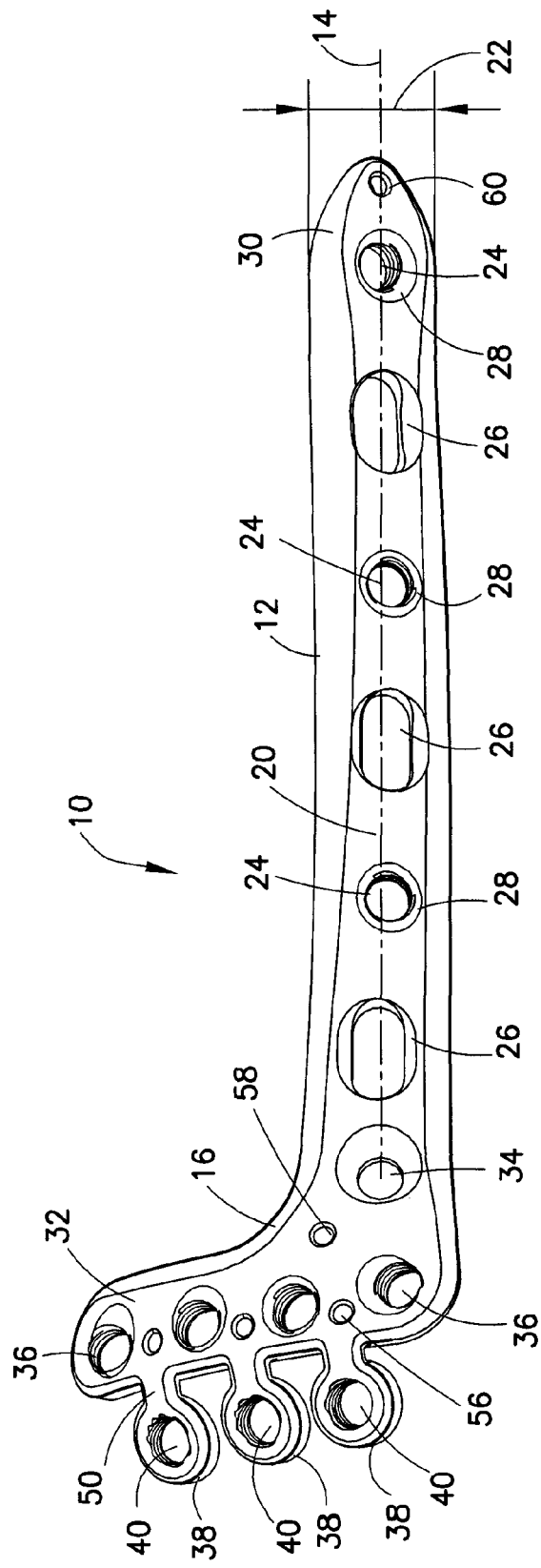
FIG. 1 is a top perspective view of an anterolateral plate of the distal tibia system of the invention.

The distal tibia plating system according to the invention includes an anterolateral plate 10 (FIGS. 1-6), a medial plate 110 (FIGS. 7-11), drill guides 200 (FIG. 12-13), bending tools 300 (FIGS. 5-6), a plate holder 400 (FIGS. 14-23), fasteners 500, 600, 700, 800 (FIGS. 24-27), and K-wires, as discussed below.

Anterolateral Plate

Figure 2:
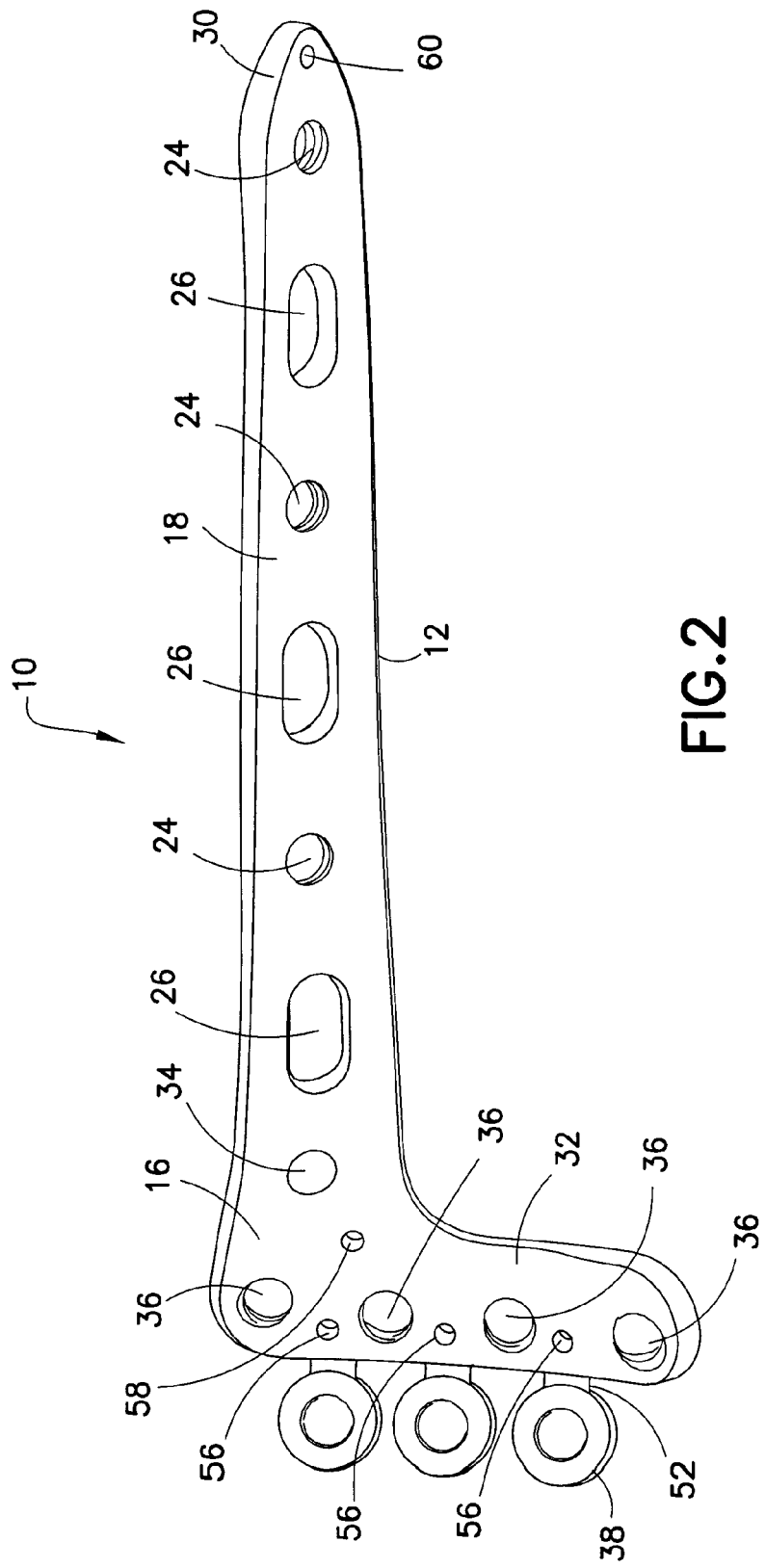
FIG. 2 is a bottom perspective view of the anterolateral plate of FIG. 1.

Turning now to FIGS. 1 and 2, the anterolateral plate 10 of the distal tibia plating system according to the invention is shown. The anterolateral plate 10 includes a shaft 12 with a longitudinal axis 14, and a distal head 16, and a lower bone contacting surface 18 and an opposite upper surface 20.

The shaft 12 is twisted about the longitudinal axis 14 to match the anterolateral bone surface of the distal tibia. The shaft 12 has a width 22 of between approximately 11 mm-12.2 mm to minimize the profile of the shaft. The shaft 12 has both threaded fastener holes 24 and elongate compression slots 26 longitudinally arranged along its length. The shaft 12 is provided with a preferably alternating arrangement of the threaded fastener holes 24 and slots 26. The number of threaded fastener holes 24 and compression slots 26 is generally dictated by the length of the shaft 12 which can vary depending on the length of the fracture being treated and the stability required. It is preferred that a threaded fastener hole 24 be provided at the proximal end of the plate. At certain plate lengths, this may result in the plate having two consecutive threaded fastener holes 24 at the proximal end (see, e.g., plate 10a in FIG. 5). The threaded fastener holes 24 are preferably triple lead tapered holes, and chamfered at 28 to permit the head of a fastener, described below, to seat lower in the plate 10. The proximal end 30 of the shaft is tapered in width to facilitate percutaneous minimally invasive insertion of the plate.

Figure 3:
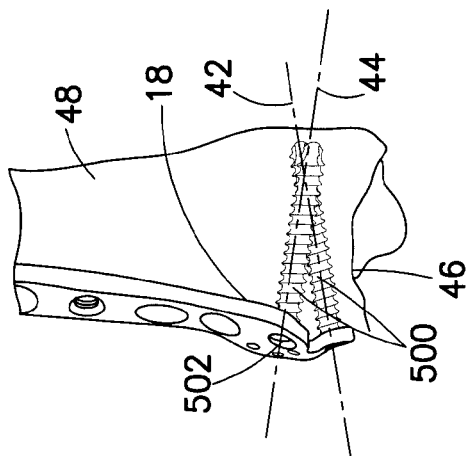
FIG. 3 is a transparent posterior view of the distal tibia with the anterolateral plate of FIG. 1 attached thereto by a plurality of fasteners.

The distal head 16 widens relative to the shaft 12 to transition into a lateral extension 32. The head 16 is preferably provided in sizes of approximately 33.5 to 38.5 mm in width, depending on anatomical considerations, to provide sufficient support in a minimized profile. The lower surface 18 of the head 16 is preferably curved in the medial-lateral direction to wrap around the distal tibia. The head 16 includes a non-threaded compression screw hole 34 and a first row of preferably four threaded fastener holes 36 having the same thread structure as holes 24. A plurality of distal tabs 38 (preferably two or three tabs) are coupled to the distal head. Each tab has a threaded hole 40 with the same thread structure as holes 24 and 36. Holes 40 are together aligned to define a second row of threaded fastener holes. The first and second rows of threaded holes 36, 40 are approximately parallel and the threaded holes 40 of the second row are staggered (transverse to the longitudinal axis 14) with respect to the threaded holes 36 of the first row. The axial arrangement of the first and second rows is such that thread axes 42 through the threaded holes of the second row converge in a proximal-distal direction below the bone contacting surface 18 of the plate relative to the thread axes 44 through the threaded holes of the first row, and that such thread axes 42 through the second row pass between the thread axes 44 through the first row. Referring to FIG. 3, this arrangement of thread axes allows fasteners 500 (generally, but any of the fixed angle fasteners discussed herein) inserted along the thread axes 42, 44 to form a load-bearing scaffold to support the articular surface 46 of the distal tibia 48 against the talus of the foot. The threaded holes in the first row are preferably chamfered so that the head 502 of fasteners 500 can seat low in the plate 10. As discussed further below, the tabs 38 are of a thinner construction than the remainder of the head 16 of the plate. The threaded holes 40 in the tabs 38 are preferably not chamfered so that the tabs have sufficient structural support to engage a selected fastener.

Figure 4:
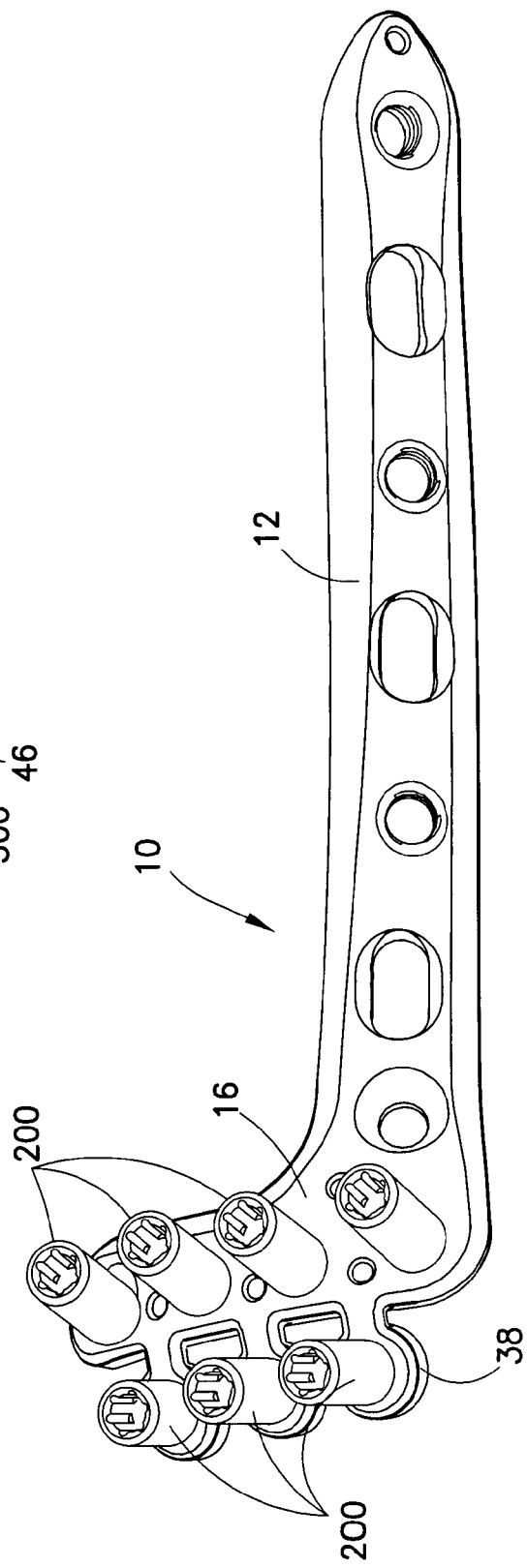
FIG. 4 is a top perspective view of the anterolateral plate of FIG. 1 shown with drill guides attached thereto.

Referring to FIG. 4, each of the threaded fastener holes can be provided with a pre-assembled drill guide 200, described in more detail below with respect to FIGS. 12 and 13, that is adapted to guide a drill into bone in axial alignment with the fastener hole. Referring to FIGS. 5 and 6, each drill guides 200 is adapted to couple relative to one member of a pair of bending tools 300 to re-orient the configuration of the tabs by the surgeon, also described in more detail below. It is preferable that each such fastener hole 40 in the second row be provided with a drill guide 200, and that the other fastener holes optionally be provided with such drill guides.

Referring to FIGS. 1-3 and 6, each distal tab 38 is ring-shaped and is connected to the distal end of the head 16 of the plate 10 with a bridge 50. The tabs 38 are preferentially bendable to customize the load bearing support of the articular surface 46 of the distal tibia 48. The bridge 50 of each tab 38 is configured to bend preferentially in rotation about the y-axis. To that end, each bridge 50 preferably has a rectangular cross-section, with width greater than thickness. In addition, the bridges may include a lower recess 52 in the widthwise direction. Then if bent, the new thread axis 42 of a fastener hole 40 will not intersect the thread axis 44 of a threaded fastener hole 36 of the first row in the head portion. To effect bending, the bending tools 300 are fit over (as shown) or into two adjacent drill guides 200, one located in a tab 38 and one located in a thread hole 36 of the first row. Force is applied to the proximal ends of the bending tools 300 to effect bending of the tab 38 relative to the head portion 16 of the plate 10. Thus, one or more of the tabs 38 can be easily reconfigured relative to the of the plate, e.g., to capture the distal rim of the tibia, to capture a specific bone fragment or buttress and support a desired area. Tab bending may easily be effected while the plate is on the bone. Further, by designing the area of the tab 38 around the fastener hole 40 thicker than the bridge 50, it is ensured that the hole 40 and threads thereof are not deformed when bending a tab 38 to a desired orientation. Moreover, the lower recess 52 also facilitates removing a tab 50 with the bending tools 300 by reverse bending the tab 38 until a clean fracture of the bridge 50 is effected. The tabs 38 are purposefully designed to fracture upon application of 20-25 in-lb force, i.e., by bending each of tabs 38 down about 30 degrees and back up about 30 degrees.

The anterolateral plate includes K-wire alignment holes 56, 58, 60 that receive K-wires for provisional fixation of bone fragments and for fluoroscopic confirmation of the location of the plate. First alignment holes 56 are preferably provided in the head portion of the plate between the threaded holes 38 of the first row, a second alignment hole 58 is provided between the first row of threaded holes 38 and the compression hole 34, and a third alignment holes 60 is provided at the proximal end 30 of the plate 10. Each K-wire alignment hole preferably provides fixed angle alignment to a K-wire inserted therethrough. K-wires (not shown) are preferably provided with the system for use with the anterolateral plate 10, as well as the medial plate 110, discussed below.

Medial Plate

Figure 7:
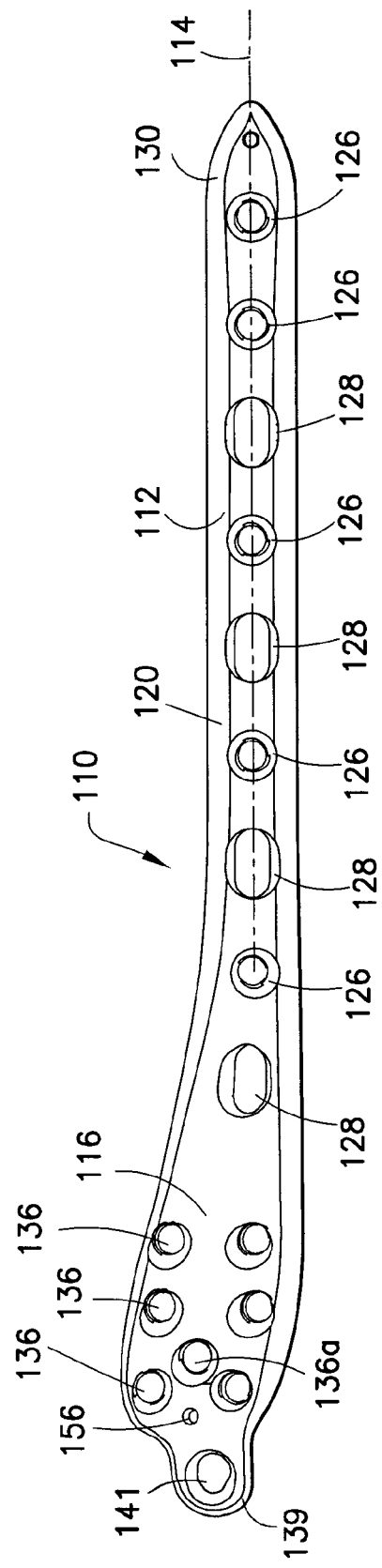
FIG. 7 is a top perspective view of a medial plate of the distal tibia plating system of the invention.

Referring to FIGS. 7 through 9, the medial plate 110 includes a shaft 112 with a longitudinal axis 114 and a relatively broader distal head 116. The shaft 112 has a shallow radius of curvature transverse to the longitudinal axis. This shallow radius enable the shaft to have a thickness that is approximately 25 percent thinner than competitive plates. The shaft 112 includes an arrangement of both threaded fastener holes 124 and compression slots 126, along its length, similar to the anterolateral plate 10. The threaded fastener holes 124 are preferably triple lead tapered thread holes. The proximal end 130 of the plate may include consecutive threaded fastener holes. The most distal slot 128a includes a peripheral undercut 133a, discussed in more detail below.

Figure 11:
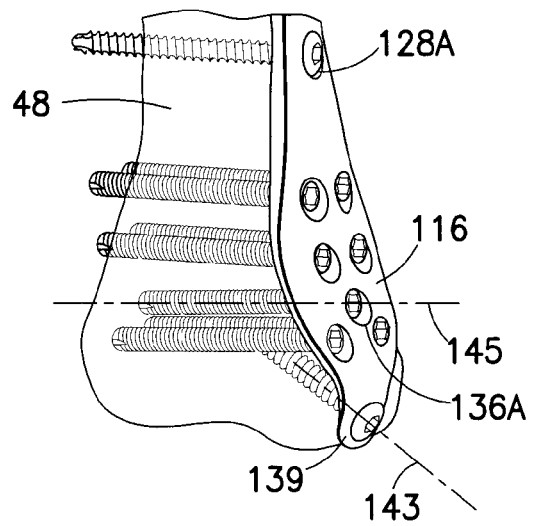
FIG. 11 is a transparent posterior view of the distal tibia with the medial plate of FIG. 7 attached thereto by a plurality of fasteners.

The head 116 of the plate 110 includes preferably seven threaded fastener holes 136 having the same hole and thread structure as holes 124. The holes 136 preferably parallel axes, and preferably arranged in two substantially parallel proximal-distal rows 135, 137 of three and a central hole 136a located between the two rows. At the distal end of the head, an extension 139 is provided with a non-threaded, non-circular hole 141 which can be used to direct a compression screw along axis 143 towards the thread axis 145 of the central hole 136a (FIG. 11). Each of the threaded holes is preferably of the same size and structure as the threaded holes in the anterolateral plate 10. In addition, each of the threaded holes in at least the head 116 is preferably provided with a drill guide 200 for guiding a drill. The drill guide 200 is described in more detail below with respect to FIGS. 12 and 13.

Figure 10:
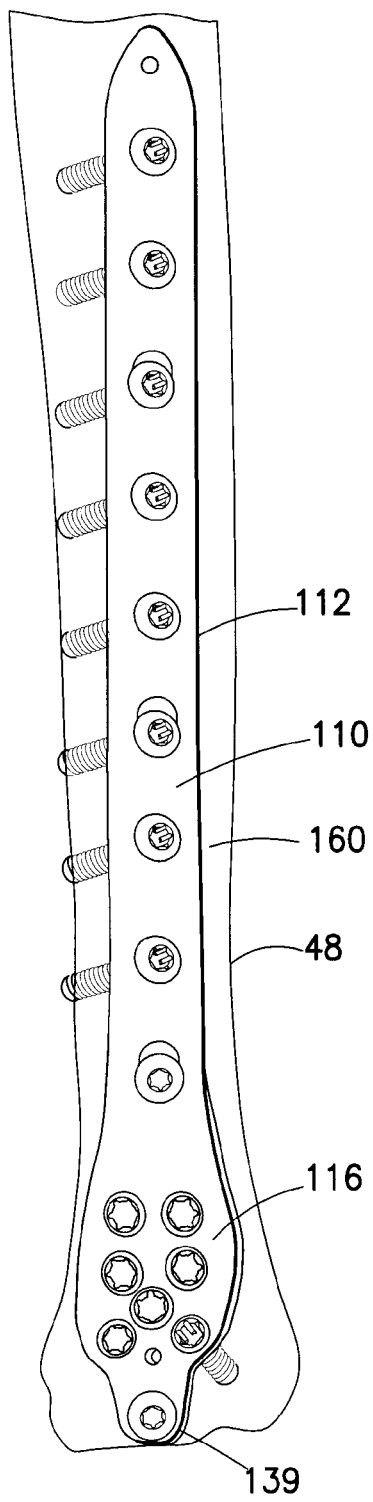
FIG. 10 is a transparent medial view of the distal tibia with the medial plate of FIG. 7 attached thereto by a plurality of fasteners.

A first K-wire alignment hole 156 is provided between the central hole 136a and the non-circular hole 141 and a second K-wire alignment hole 160 is provided at the proximal end 130 of the shaft 112 to facilitate alignment and temporary positioning of the plate on the bone. FIGS. 10 and 11 show the medial plate implanted on the medial side 160 of the distal tibia 48.

Each of the plates 10, 110 of the present system may be formed from any one of numerous materials known in the art, including a stainless steel, a titanium and a titanium alloy such as Ti-6Al-4V. More preferably, each of the plates is preferably machined from a solid round bar of Ti-6Al-4V-ELI in the fully annealed condition. Each plate is machined to its respective anatomical shape to ensure minimal work hardening. After machining, the parts are polished and anodized. The resulting plate material is fully 'soft' and permits the ability to bend the plate at the tabs or relative to the longitudinal axis without fracture of the plate. In general, each of the plates described herein is significantly thinner than currently available plates for the same types of fractures, yet still has the appropriate rigidity for internal fixation of the fractured bone.

Drill Guides

Figure 12:
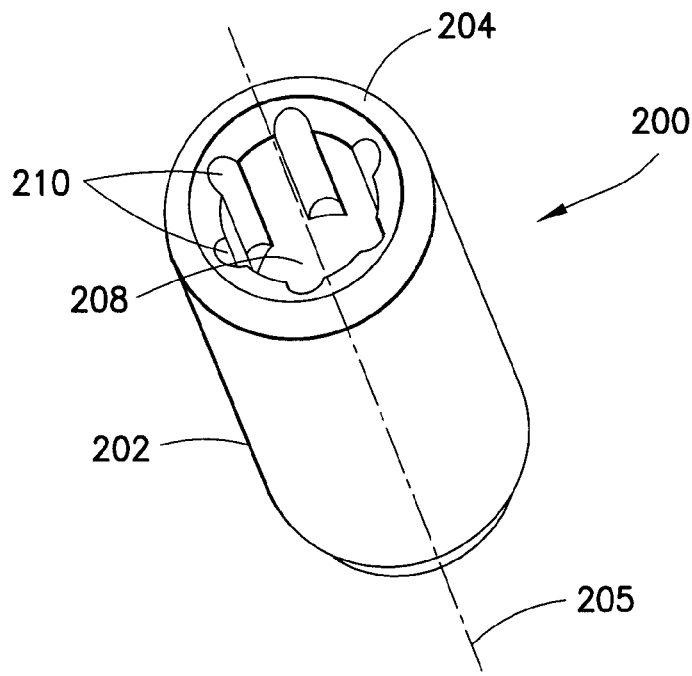
FIG. 12 is a top perspective view of drill guide for use with the distal tibia plating system of the invention.
Figure 13:
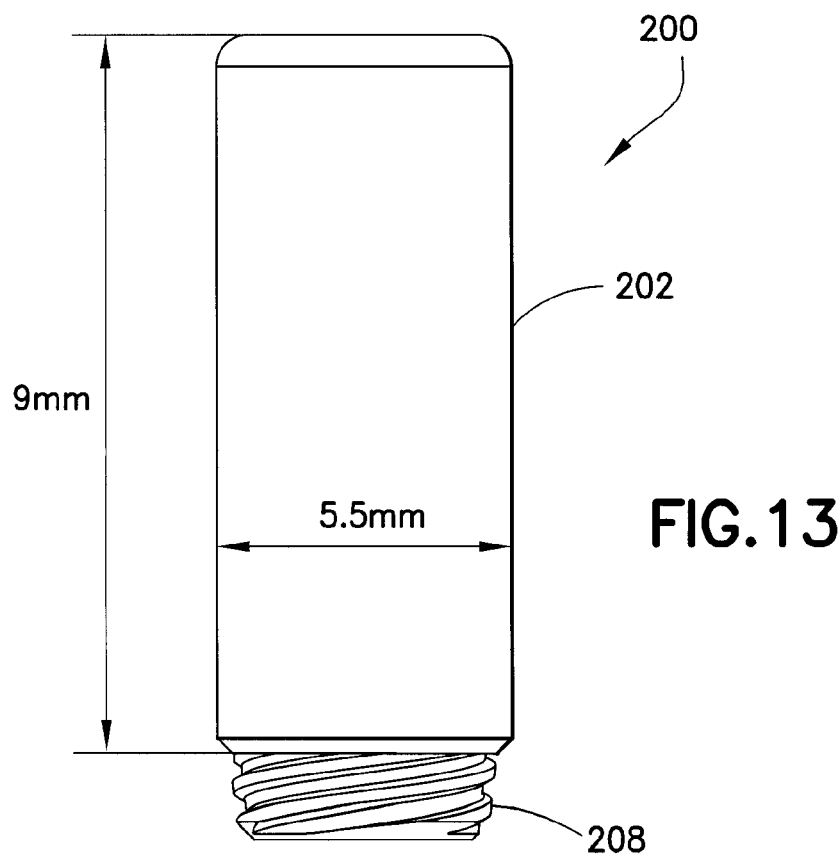
FIG. 13 is a side elevation of the drill of FIG. 12.

Referring to FIGS. 12 and 13, a drill guide 200 having a cylindrical body 202, a proximal end 204, and a distal end 206 is shown. The drill guide 200 also has an axis 205 and a longitudinal bore 208 sized for guiding a conventional bone drill. A plurality of internal drive elements 210 are formed in bore 208 near proximal end 204. In this embodiment, the plurality of internal drive elements 210 include six internal drive elements 210 for receiving the hexagonally shaped distal tip of a conventional bone screw driver tool, although other configurations and quantities of internal drive elements 210 are possible.

The distal end 208 of the drill guide 200 is provided with a tapered threaded portion 212 configured for threaded engagement with a tapered threaded hole of both the anterolateral or medial bone plates, such that axis 205 is collinear with the axis of the tapered threaded hole.

The cylindrical body 202 preferably has a length of approximately 9 mm from the proximal until the start of the threaded portion 212, and an external diameter of approximately 5 mm.

The bone plates 10, 110 may be provided to the surgeon with each tapered threaded hole of the bone plate already preassembled with drill guide (or guides preassembled in selected threaded holes), so that it is not necessary for the surgeon or an assistant to attach a drill guide to each hole during the procedure as is normally done for conventional bone plating systems. In this way, the surgeon may quickly drill several bone holes, such that the axis of each hole is in perfect alignment with the hole thread axis. The surgeon may then remove the drill guide using the hexagonally tipped driver and insert a locking bone fastener, such that the threaded head of the locking fastener easily engages with the threaded hole. The pre-assembly of a drill guide to a bone plate is described in co-owned U.S. Pub. No. 20060149250A1, and the use of such drill guide for bending a plate is described in co-owned U.S. Pub. No. 20060161158A1, 20070233111A1, and 20070233112A1, all of which are hereby incorporated by reference herein in their entireties.

The drill guides are preferably color coded, so to provide a visual cue to the surgeon and staff as to whether a plate is for the left or right bone. For example, guides may be color green for left application and red for right application.

Plate Holder

Figure 14:
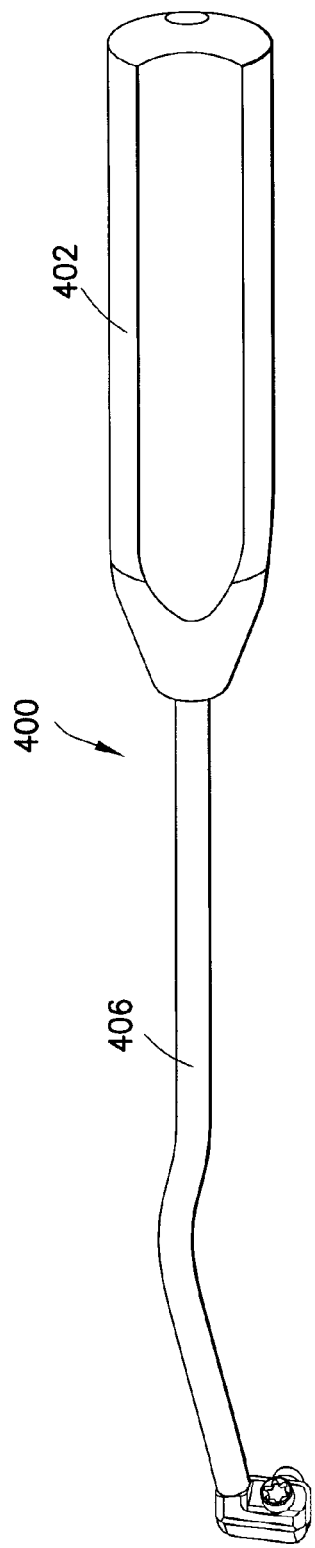
FIG. 14 is a perspective of a plate holder according to the invention.
Figure 15:
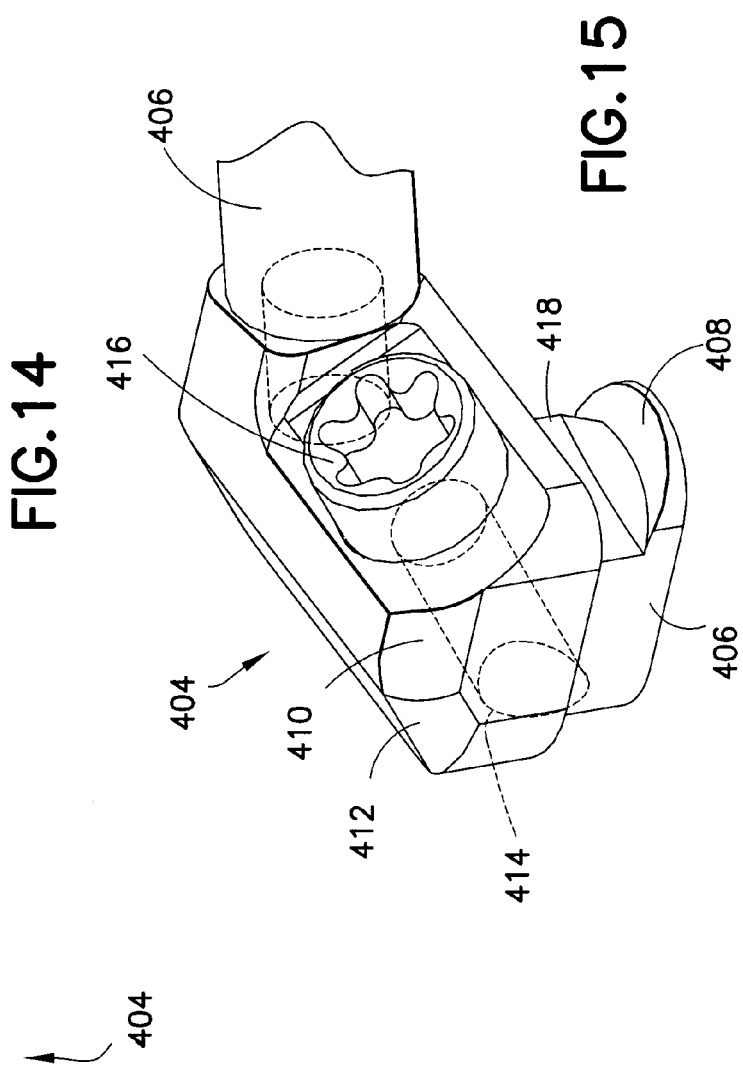
FIG. 15 is an enlarged distal end broken view of the plate holder of FIG. 14.
Figure 20:
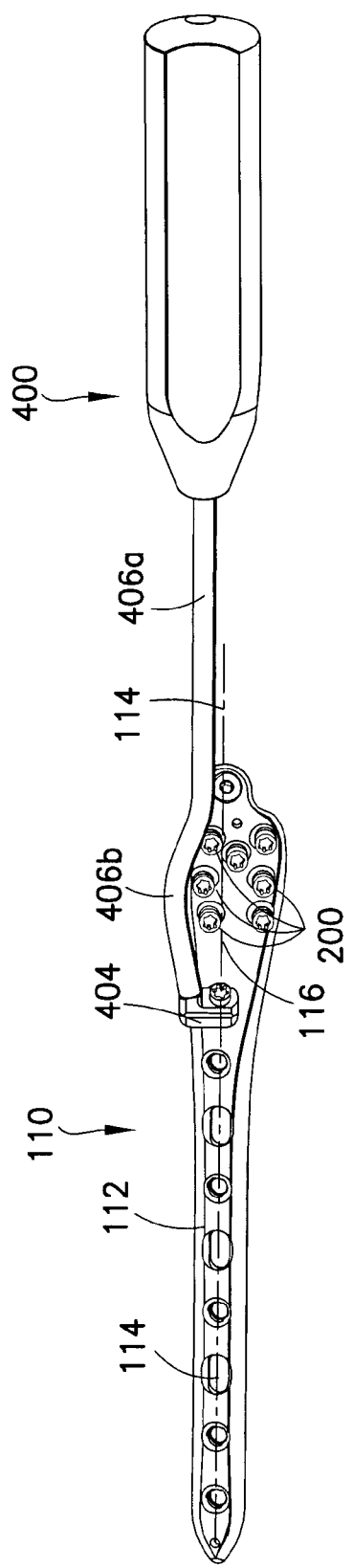
FIG. 20 is a medial view of the medial plate and plate holder assembly.
Figure 21:
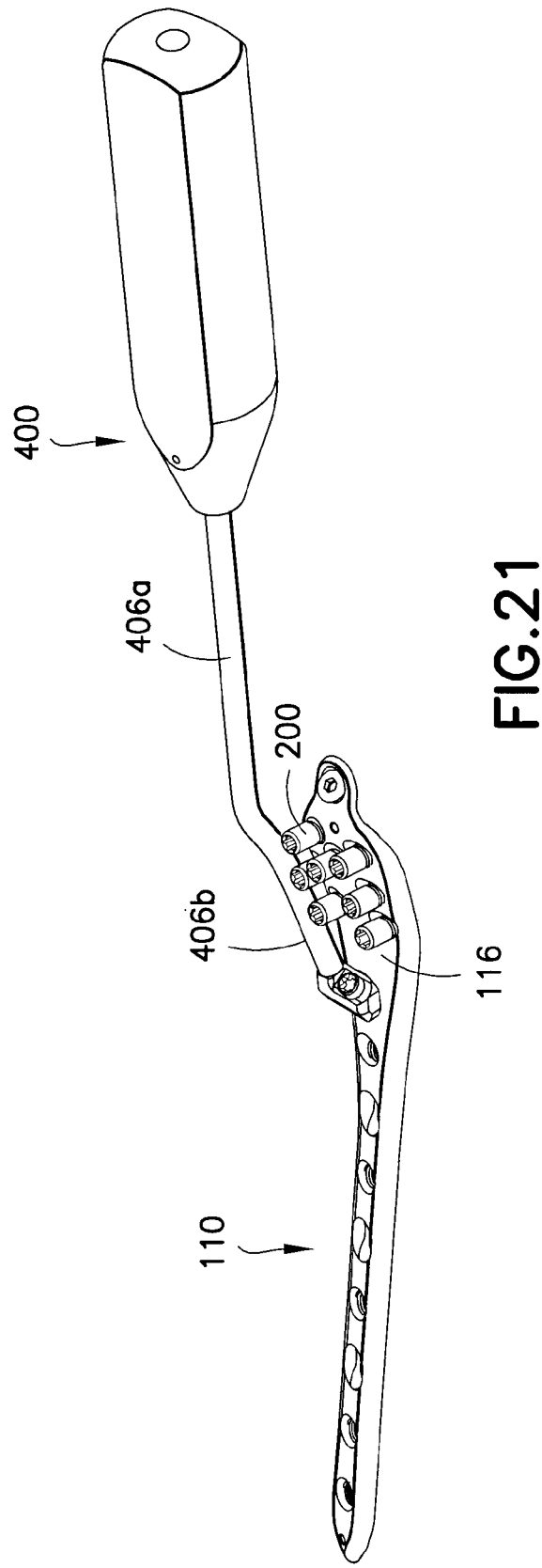
FIG. 21 is a distal perspective view of the assembly of FIG. 20.
Figure 22:
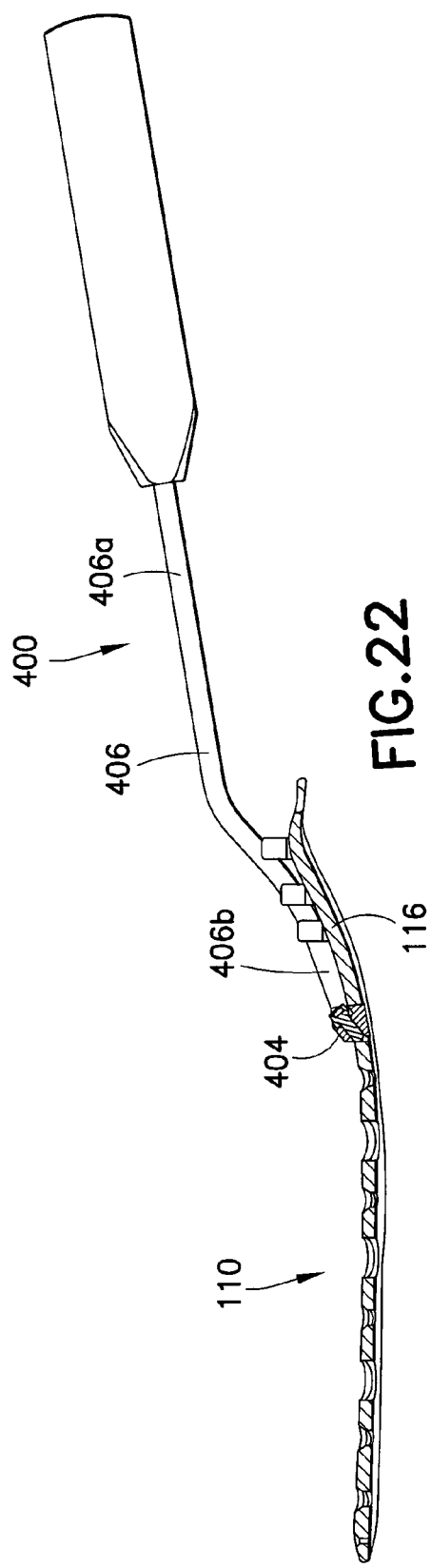
FIG. 22 is section view through the longitudinal axis of the medial plate of the assembly of FIG. 20.
Figure 23:
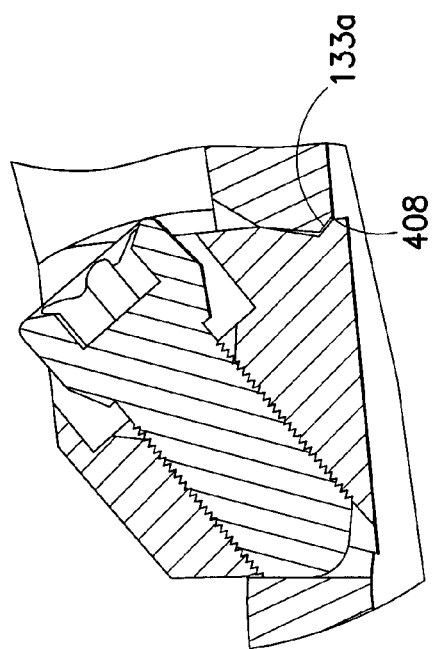
FIG. 23 is an enlarged section view through the coupling of the plate holder to the medial plate.

Referring to FIGS. 14 and 15, a plate holder 400 is also provided which can be coupled to the plates 10, 110 to maneuver the plates subcutaneously through a minimally invasive surgical incision. The plate holder 400 includes a handle 402, a mount 404, and an arm 406 extending between the handle 402 and the mount 404. The mount 404 includes a first portion 406 with a lip 408 which seats within a distalmost compression slot on the shaft of either plate, and a second portion 410 at which the arm is permanently secured. The second portion 410 includes a tapered proximal side 412 to ease insertion under soft tissue. A set screw hole 414 is provided through the first and second portions, and a set screw 416 is provided therein. When the first portion 406 is seated in a slot of a plate shaft and the set screw 416 is driven to seat, the set screw drivers the first portion 406 into compression with the plate shaft to lock the holder 400 and plate into an assembly. The arm 406 of the plate holder 400 is contoured to seat closely to the head of the respective plate, but to clear the drill guides 200 in the head portion of the plates. The plate holder facilitates positioning of the plate on the bone surface and holding the plate while the first fastener is inserted.

More particularly, referring to FIGS. 16 through 19, the plate holder 400 is shown coupled to the anterolateral plate 10. In the anterior view, the proximal portion 406a of the arm 406 (adjacent the handle) of the holder 400 extends in the same plane as the longitudinal axis 14 of the shaft 12 of the plate 10. The distal portion 406b of the arm (adjacent the plate) is contoured about the head so as to not interfere with the drill guides 200 but to extend close to the plate (see vertical dimension in FIG. 18) to limit interference with soft tissue during plate insertion. When the mount 404 is coupled relative to the plate, the lip 408 does not extend under the compression slot 26 of the plate 10. The set screw 416 forces a distal wall 418 of the first portion 406 against a wall of the slot to engage the holder 400 relative to the plate. The holder 400 may be released from the plate by loosening the set screw. The angle of the set screw hole 414 and set screw 416 is approximately 35° so as to effect appropriate compression and be easily accessed via a driver even once the plate is at the implantation site.

Referring to FIGS. 20 through 23, the same plate holder 400 is shown attached to the medial plate 110. The proximal end 406a of the arm 406 is also in-plane with the shaft axis 114, and the distal end 406b is contoured about the head 116 so as to not interfere with drill guides 200 and to maintain a low profile to the plate. The distal compression slot 126a of the medial plate includes an undercut 133a. When the first portion of the mount is inserted into the slot 126a, the lip 408 engages at the undercut 133a to further secure the holder to the plate 110.

Plate holders 400 may be color coded for left and right plates (e.g., green-left; right-right) and correspond in color to the drill guides to facilitate engagement to the correct plate.

Fasteners

Each of the threaded holes in both plates 10, 110, whether in the head or shaft portions of the anterolateral or medial plate can all receive the same fastener types. Thus, the fasteners in the system are interchangeable between the plates. Generally, the fasteners includes a shank portion for engagement into the bone, wherein the shank portion may have one of a cortical thread, a cancellous thread, a non-threaded portion and combinations thereof. Each fastener type further includes a head portion for engagement with the fastener hole, wherein the head portion may have one of a fixed angle locking head, a non-locking compression head and a multi-directional locking head.

Figure 24:
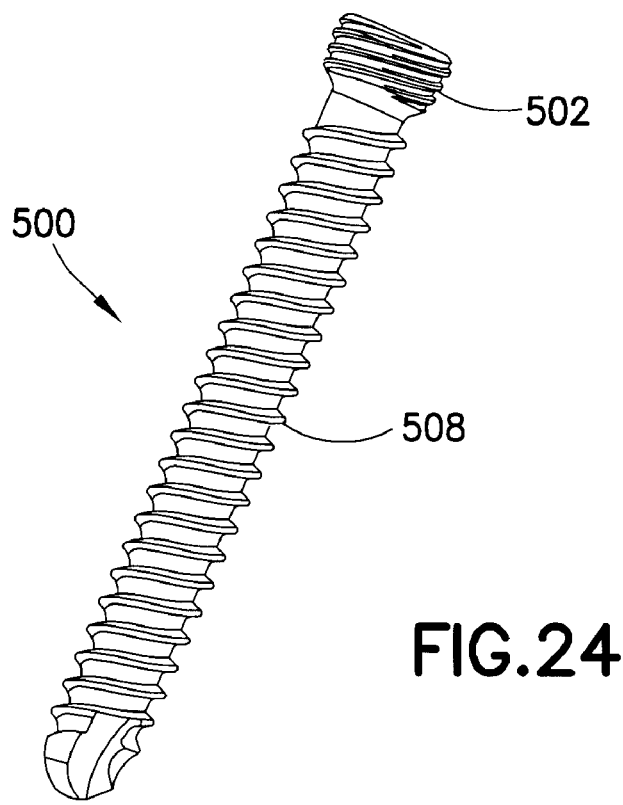
FIG. 24 is side elevation view of a fixed angle locking cortical screw for use with the bone plates of the distal tibia system of the invention.
Figure 25:
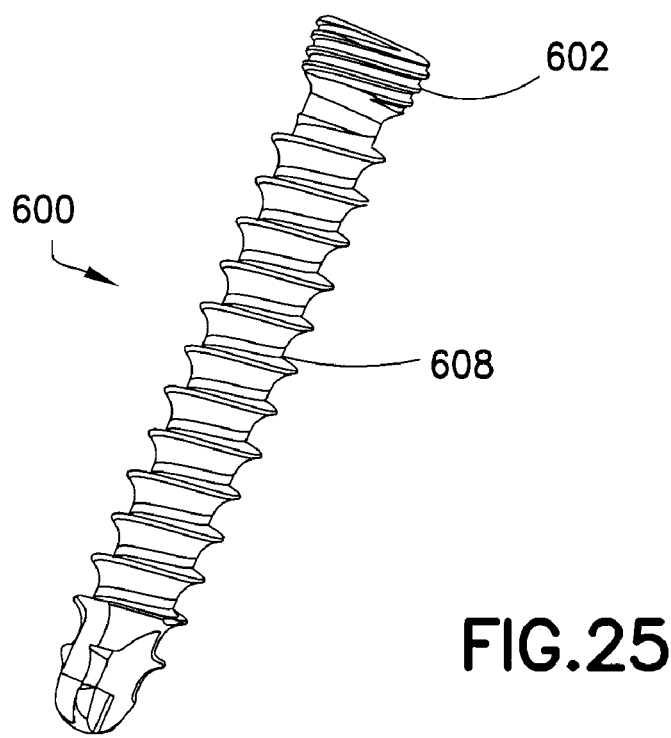
FIG. 25 is side elevation view of a fixed angle locking cancellous screw for use with the bone plates of the distal tibia system of the invention.

FIGS. 24 through 27 show four embodiments of fixed angle bone fasteners. FIG. 24 is a side view of a fixed angle locking screw 500, which includes a tapered threaded head 502 having a driver recess (not shown), and a threaded shaft 504. The threads on the shaft having a pitch adapted for engaging cortical bone. Screw 500 may be inserted and locked into a tapered, threaded hole of a bone plate at a fixed angle predetermined by the hole thread axis. FIG. 25 is a side view of a fixed angle locking screw 600, substantially similar to screw 500, but wherein the threads of shaft 604 have a relatively larger pitch adapted for engaging cancellous bone.

Figure 26:
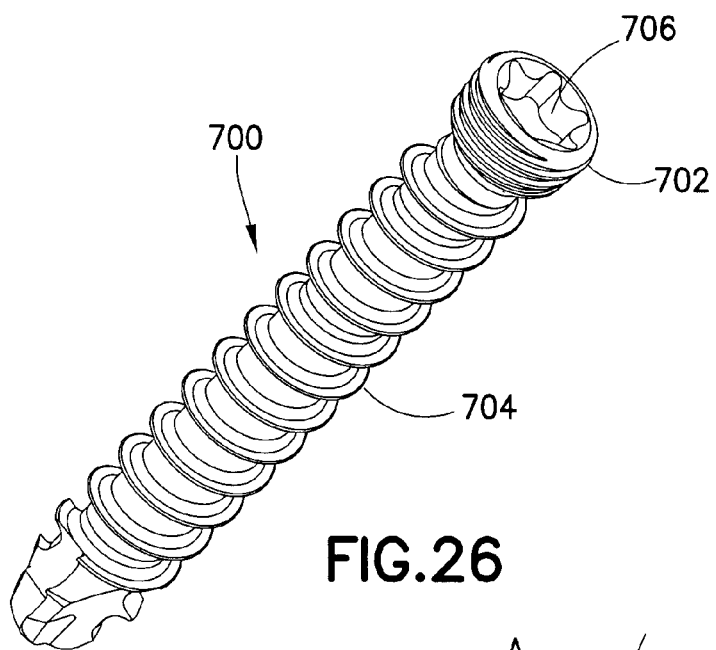
FIG. 26 is perspective view of a multidirectional locking screw for use with the bone plates of the distal tibia system of the invention.

FIG. 26 is a side view of a multidirectional locking screw 700. Screw 700 includes a head 702 with a square drive recess 706, and a shaft 704. The screw 700 may be locked into either plate, such that a screw axis forms an angle in the range of 0-15 degrees with the thread axis of the hole. Screw 700 may be formed from a cobalt-chrome alloy that is significantly harder than the plate material, which may be a titanium alloy. Such a multidirectional locking screw is described in detail in U.S. Pub. No. 20070088360A1, which is hereby incorporated by reference herein in its entirety.

For the fastener embodiments 500, 600, and 700, the shaft alternatively be smooth along all or a portion of its length.

Figure 27:
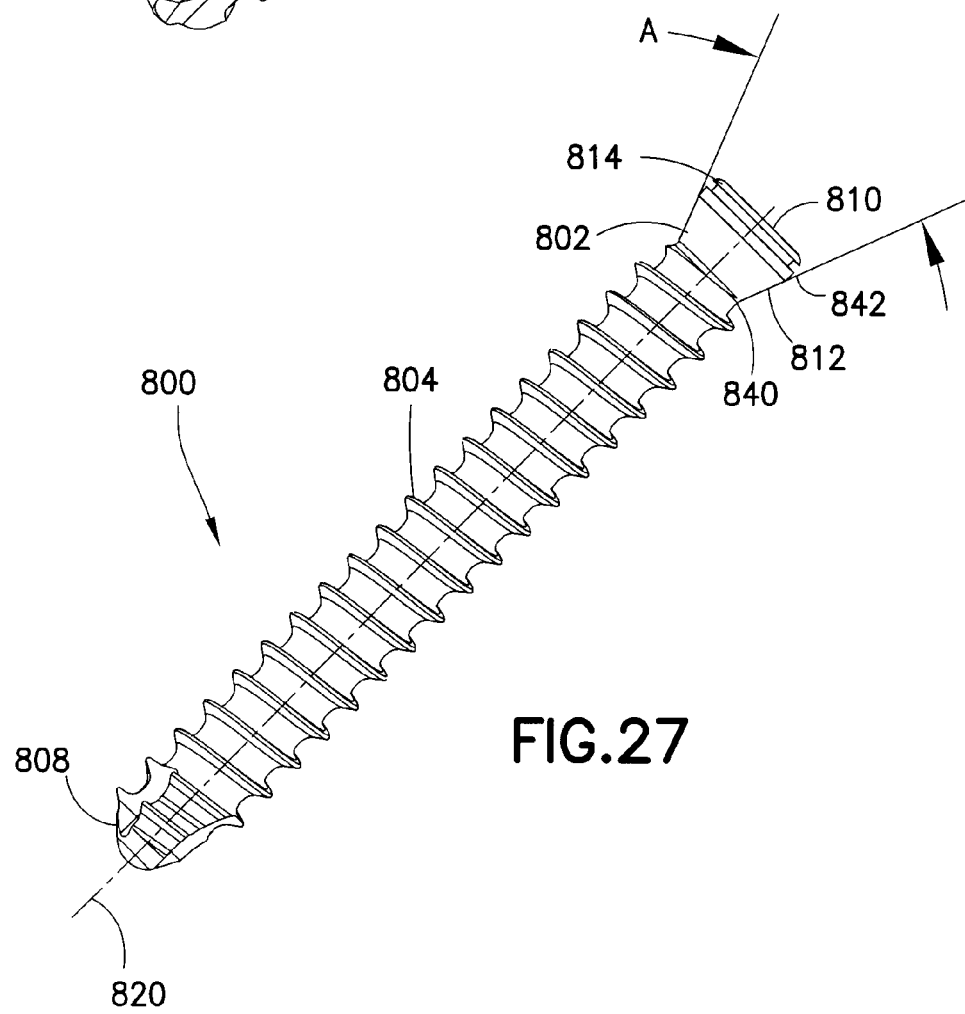
FIG. 27 is side elevation view of a multidirectional compression fastener for use with the bone plates of the distal tibia system of the invention.

FIG. 27 is a multidirectional compression fastener 800, also called screw 800. Screw 800 includes a threaded shaft 804 and a distal tip 808. Screw 800 further includes a head 802 having a proximal face 810 with a square drive recess, although other drive recess configurations are possible. Head 802 includes a smooth, frustoconical portion 812 having a small diameter end 840 attached to body 804 and a large diameter end 842 forming a peripheral edge 814 of proximal face 810. Frustoconical portion 812 has an included angle (indicated by A) centered on a screw axis 820. Peripheral edge 814 may have an external radius. Threads of screw shaft 804 may be either cancellous or cortical, and may optionally be formed along only a portion of the length of the shaft 804.

As will be appreciated by those skilled in the art, the present system described herein provides to a surgeon the advantageous option to use any one of a standard compression screw (no shown, but for use through non threaded holes), a fixed angle locking screw (screws 500, 600), a multidirectional locking screw (screw 700), or a multidirectional compression screw (screw 800) in the same tapered threaded hole, which is included in both of the bone plates described herein. In addition, each of screws 600, 600, 700, 800 is insertable into the tapered threaded hole, such that the screw head is minimally proud relative to the top surface of the bone plate, thereby minimizing patient discomfort and complications due to soft tissue irritation.

In view of the above, the system facilitates diaphyseal, metaphyseal, and subchondral support of the articular surface of the distal tibia so that plate shares the load with bone during healing. The system also facilitates bone targeting and contouring of the plates to the bone so that intra-articular fragments can be captured and fixatied. The system accomplishes this in a manner that is low profile to minimize soft tissue trauma and patient discomfort.

There have been described and illustrated herein several embodiments of plates of a distal tibia plating system. While particular embodiments of the invention have been described, it is not intended that the invention be limited thereto, as it is intended that the invention be as broad in scope as the art will allow and that the specification be read likewise. Where the terms 'approximate', 'approximately' or 'substantially' are used herein, such terms are to be defined as ±20 percent of a given number, amount, or relative position or location, as determined by context. It will therefore be appreciated by those skilled in the art that yet other modifications could be made to the provided invention without deviating from its spirit and scope as claimed.

What is claimed is:

1. An anterolateral plate for the anterolateral surface of the distal tibia, comprising:
   a) a shaft twisted about its longitudinal axis and including a plurality of threaded holes and a plurality of elongate compression slots longitudinally displaced relative to said axis, each of the threaded holes and compression slots for receiving a respective bone fastener, the shaft having a proximal end tapered in width;
   b) a distal head that widens relative to the shaft to transition into a lateral extension extending only on one side of said shaft, the head including a proximal non-threaded hole, and a first row of four threaded holes with two of said holes located in said lateral extension; and
   c) a plurality of distal tabs connected to a distal end of the distal head, each of the tabs including a threaded hole and connected to the distal end of the head by a deformable bridge, the tabs including a ring portion in which the threaded hole is defined, the ring portion having a first thickness, and the distal head having a second thickness greater than the first thickness,
   the threaded holes in the tabs together defining a second row of threaded holes capable of receiving the same fasteners as the threaded fastener holes of the first row, the first and second rows being approximately parallel, and the threaded fasteners holes of the second row being staggered transverse to the longitudinal axis in an alternating manner with respect to the threaded holes of the first row, and the arrangement of the first and second rows is such that thread axes through the fastener holes in the second row converge in a proximal-distal direction below a bone contacting surface of the plate relative to thread axes through the fastener holes in the first row, and that such thread axes through the fastener holes of the second row pass between the thread axes of the fastener holes through the first row so as to form a load-bearing scaffold to support the articular surface of the distal tibia.

2. An anterolateral plate according to claim 1, wherein:
each bridge has a rectangular cross-section with a width greater than a thickness.

3. An anterolateral plate according to claim 1, wherein:
at least one bridge defines a lower recess in a widthwise direction.

4. An anterolateral plate according to claim 1, wherein:
at least one tab is designed to fracture at the bridge upon application of 20-25 in-lb force.

5. An anterolateral plate according to claim 1, wherein:
the threaded holes in the shaft and distal head are chamfered, and the threaded holes in the tabs are not chamfered.

6. An anterolateral plate according to claim 1, further comprising:
a plurality of distinct guides, wherein each of the threaded holes of the first and second rows are pre-assembled with one of the distinct guides for guiding a drill.

7. An anterolateral plate according to claim 1, wherein:
each of the threaded holes in the first row, the second row and the shaft are configured to receive the same fasteners.

8. An anterolateral plate according to claim 1, wherein:
the shaft is provided with an alternating arrangement of the threaded holes and the slots.

9. A distal tibia plate system for the distal tibia, comprising:
a) a medial plate configured for the medial side of the distal tibia, including
   i) a shaft having a longitudinal axis and including a plurality of tapered triple lead first threaded holes and a plurality of elongate compression slots longitudinally displaced relative to said axis, each of the threaded holes and compression slots for receiving a respective bone fastener, the shaft having a proximal end tapered in width, and
   ii) a distal head broader than the shaft, the head including an arrangement of seven tapered triple lead second threaded holes provided with parallel axes defined within the boundary of the head, and a distal extension extending from the distal end of the plate and provided with a non-threaded oblong hole oriented in an as-manufactured configuration to direct a fastener in a generally proximal direction;

b) a fixed angle fastener having a tapered threaded head and a shaft, the head sized to be engaged in each of the first and second threaded holes;

c) a multidirectional locking fastener having a threaded head and a shaft, the head being made of a harder material than the medial plate and sized to be engaged in each of the first and second threaded holes; and d) a compression fastener having a frustoconical head and a shaft, the head sized to be received in each of the first and second threaded holes.

10. A distal tibia plating system according to claim 9, further comprising:

an anterolateral plate including, i) a shaft having a longitudinal axis, the shaft twisted about the longitudinal axis, the shaft including a plurality of threaded holes and a plurality of elongate compression slots longitudinally displaced relative to said axis, each of the threaded holes and compression slots for receiving a respective bone fastener;

ii) a distal head that widens relative to the shaft to transition into a lateral extension only on one side of said shaft, the head including a proximal non-threaded hole, and a first row of a plurality of threaded holes with two of said holes located in said lateral extension; and iii) a plurality of distal tabs connected to a distal end of the distal head, each of the tabs including a threaded hole and connected to the distal end of the head by a deformable bridge, the threaded holes in the tabs together defining a second row of threaded holes capable of receiving the same fasteners as the threaded fastener holes of the first row, the first and second rows being approximately parallel, and the threaded fasteners holes of the second row being staggered transverse to the longitudinal axis in an alternating manner with respect to the threaded holes of the first row, and the arrangement of the first and second rows is such that thread axes through the fastener holes in the second row converge in a proximal-distal direction below a bone contacting surface of the plate relative to thread axes through the fastener holes in the first row, and that such thread axes through the fastener holes of the second row pass between the thread axes of the fastener holes through the first row so as to form a load-bearing scaffold to support the articular surface of the distal tibia.

11. A distal tibia plating system according to claim 9, further comprising:

a plurality of distinct guides, wherein each of the threaded holes in the distal head are pre-assembled with one of the distinct guides for guiding a drill.

12. A distal tibia plating system according to claim 9, further comprising:

a plate holder couplable to one of the compression slots, the plate holder including a handle, a plate mount, and an arm between the handle and the mount, the mount including a first portion extendable into a compression slot and a second portion extending thereabove, a threaded set screw hole being defined at an angle through the first and second portions, and a set screw provided in the set screw hole, the arm including a first length adjacent the handle and a second length adjacent the mount, wherein when the plate holder is coupled to the medial plate, the first length extends in a common plane with the longitudinal axis of the medial plate.

13. A distal tibia plating system according to claim 12, wherein:

the second length of the arm is contoured around the threaded holes in the distal head of the plate.

14. A distal tibia plating system according to claim 12, wherein:

the first portion includes a distal lip which seats under a distal edge of the distalmost slot in the shaft of the medial plate.

15. A distal tibia plating system according to claim 12, wherein:

the second portion includes a proximal taper.

16. A distal tibia plating system according to claim 12, wherein:

the angle is approximately 35°.

17. A distal tibia plate system for the distal tibia, comprising:

a) an anterolateral plate configured for the anterolateral side of the distal tibia, including, i) a shaft having a longitudinal axis, the shaft twisted about the longitudinal axis, the shaft including a plurality of threaded holes and a plurality of elongate compression slots longitudinally displaced relative to said axis, each of the threaded holes and compression slots for receiving a respective bone fastener, ii) a distal head that widens relative to the shaft to transition into a lateral extension only on one side of said shaft, the head including a proximal non-threaded hole, and a first row of a plurality of threaded holes with two of said thread holes located in said lateral extension, and iii) a plurality of distal tabs connected to a distal end of the distal head, each of the tabs including a threaded hole and connected to the distal end of the head by a deformable bridge, the threaded holes in the tabs together defining a second row of threaded holes capable of receiving the same fasteners as the threaded fastener holes of the first row, the first and second rows being approximately parallel, and the threaded fasteners holes of the second row being staggered transverse to the longitudinal axis in an alternating manner with respect to the threaded holes of the first row, and the arrangement of the first and second rows is such that thread axes through the fastener holes in the second row converge in a proximal-distal direction below a bone contacting surface of the plate relative to thread axes through the fastener holes in the first row, and that such thread axes through the fastener holes of the second row pass between the thread axes of the fastener holes through the first row so as to form a load-bearing scaffold to support the articular surface of the distal tibia;

b) a medial plate sized for the medial side of the distal tibia, including i) a shaft having a longitudinal axis and including a plurality of tapered triple lead first threaded holes and a plurality of elongate compression slots longitudinally displaced relative to said axis, each of the threaded holes and compression slots for receiving a respective bone fastener, the shaft having a proximal end tapered in width, and ii) a distal head broader than the shaft, the head including an arrangement of seven tapered triple lead second threaded holes provided with parallel axes defined within the boundary of the head, and a distal extension extending from the distal end of the plate and provided with a non-threaded oblong hole oriented in an as-manufactured configuration to direct a fastener in a generally proximal direction;

c) a fixed angle fastener having a tapered threaded head and a shaft, the head sized to be engaged in either the first or second threaded holes;

d) a multidirectional locking fastener having a threaded head and a shaft, the head being made of a harder material than the medial plate and sized engage either of the first or second threaded holes;

e) a compression fastener having a frustoconical head and a shaft, the head sized to be received in either of the first or second threaded holes;

f) discrete drill guides pre-assembled in the threaded holes in the head and tabs of the tibia plate and the distal head of the medial plate, said pre-assembled drill guides removable from said threaded holes; and g) a pair of bending tools which couple relative to the drill guides.

18. A system according to claim 17, further comprising:
a plate holder including a handle, a plate mount at which the holder is removably couplable to either plate, and an arm extending between the handle and the mount.

19. A system according to claim 18, wherein:
left and right anterolateral plates are provided,
left and right medial plates are provided, and
the left and right plate holders are provided.

20. A system according to claim 19, wherein:
the left and right plate holders are discretely colored, and the drill guides pre-assembled in the left and right anterolateral plate and left and right medial plates are also discretely colored for left and right plates, and a first color for the left plate holder corresponds with the color of the drill guides in the left anterolateral and medial plates and second first color for the right plate holder corresponds with the color of the drill guides in the right anterolateral and medial plates.

* * * * *